United States Patent
Zhao et al.

(10) Patent No.: US 10,906,858 B2
(45) Date of Patent: Feb. 2, 2021

(54) CTA SOLVENT EXCHANGING METHOD

(71) Applicant: TIANHUA INSTITUTE OF CHEMICAL MACHINERY AND AUTOMATION CO., LTD, Gansu (CN)

(72) Inventors: Xu Zhao, Gansu (CN); Zhongxin Sun, Gansu (CN); Wanyao Zhang, Gansu (CN); Tianbao Wang, Gansu (CN); Xiangnan Zhai, Gansu (CN); Yongpeng Tan, Gansu (CN); Guohai Zhang, Gansu (CN); Yu Guo, Gansu (CN); Xiaoling Xie, Gansu (CN)

(73) Assignee: Tianhua Institute of Chemical Machinery and Automation Co., Ltd, Gansu (CN)

( * ) Notice: Subject to any disclaimer, the term of this patent is extended or adjusted under 35 U.S.C. 154(b) by 0 days.

(21) Appl. No.: 16/347,170

(22) PCT Filed: May 15, 2017

(86) PCT No.: PCT/CN2017/084349
§ 371 (c)(1),
(2) Date: May 2, 2019

(87) PCT Pub. No.: WO2018/171027
PCT Pub. Date: Sep. 27, 2018

(65) Prior Publication Data
US 2020/0157034 A1 May 21, 2020

(30) Foreign Application Priority Data
Mar. 22, 2017 (CN) .......................... 2017 1 0173239

(51) Int. Cl.
*C07C 51/47* (2006.01)
*C07C 63/26* (2006.01)
*B01D 35/16* (2006.01)

(52) U.S. Cl.
CPC .............. *C07C 51/47* (2013.01); *B01D 35/16* (2013.01); *C07C 63/26* (2013.01)

(58) Field of Classification Search
None
See application file for complete search history.

(56) References Cited

U.S. PATENT DOCUMENTS

| 5,200,557 A | 4/1993 | Gee et al. |
| 2017/0081269 A1* | 3/2017 | Zhao ........................ C07C 51/47 |

FOREIGN PATENT DOCUMENTS

| CN | 102126945 A | 7/2011 |
| CN | 102476994 A | 5/2012 |

(Continued)

OTHER PUBLICATIONS

Search Report based on Chinese priority application No. 201710173239.2; dated Nov. 10, 2019.

*Primary Examiner* — Amy C Bonaparte
(74) *Attorney, Agent, or Firm* — Muncy, Geissler, Olds & Lowe, P.C.

(57) ABSTRACT

The present invention relates to a method for processing acetic acid solvent in Crude Terephthalic Acid (CTA) in an oxidized unit of a pure terephthalic acid (PTA) industrial apparatus. In the present invention, a filter cake in CTA is washed by means of a two-stage-three-step method. The present invention further shortens the production process of solvent exchanging technique of CTA pressure filters, improves production capacity of a device, reduces investment of the device, reduces energy consumption of a system, (Continued)

and solves the shortcomings of the existing CTA solvent exchanging technique of the pressure filters.

7 Claims, 3 Drawing Sheets

(56) References Cited

FOREIGN PATENT DOCUMENTS

| | | | |
|---|---|---|---|
| CN | 103121946 A | 5/2013 | |
| CN | 105237391 A | 1/2016 | |
| CN | 205061929 U | 3/2016 | |
| CN | 103936581 A | 7/2017 | |
| JP | H09-295957 A | 11/1997 | |
| JP | 2015140342 A | 8/2015 | |
| WO | WO-2015/176562 A1 | 11/2015 | |
| WO | WO-2015176562 A1 * | 11/2015 | ............. C07C 51/47 |

* cited by examiner

CTA SOLVENT EXCHANGING METHOD

FIELD OF THE INVENTION

The present invention relates to a crude terephthalic acid (CTA) solvent exchanging method, and particularly to a method for processing acetic acid solvent in CTA in an oxidising unit of a pure terephthalic acid (PTA) industrial apparatus. The method is also applicable to solvent exchanging techniques for other slurry systems.

RELATED ART

In conventional PTA industrial apparatus, CTA generated in reaction processes often contains a large number of impurities, such as acetic acid, catalyst and the like. According to processing requirements, the impurities in CTA are required to be removed before PTA refining processes.

Presently, there are mainly two kinds of CTA processing methods.

(1) One method is a processing technique using a centrifuge or a vacuum filter together with a steam pipe rotary dryer, which is now commonly used for processing CTA in the PTA industry.

FIG. 1 shows a flow chart of this processing technique using a centrifuge or a vacuum filter together with a steam pipe rotary dryer. As shown in FIG. 1, first, CTA is conveyed to a centrifuge or a vacuum filter for a preliminary separation by means of a slurry pump. After part of impurities, such as acetic acid, catalyst and the like, are removed, a filter cake is generated. Then, the filter cake is conveyed to a steam pipe rotary dryer, in which a drying process is performed on the filter case with the aid of vapor so as to further remove impurities in the filter cake. Then, the processed CTA filter cake is conveyed to subsequent refining units. However, this method has disadvantages of a long processing flow, much accessory equipments, high equipment investment, large occupied area, high energy consumption, etc., and is thus being phased out.

(2) The other method is a solvent exchanging technique which performs multiple stages of filtering and washing in a rotary pressure filter in a reversed-flow manner.

The solvent exchanging technique is a new approach for processing acetic acid solvent in CTA, and have been proposed by Tianhua Institute of Chemical Machinery and Automation Co., Ltd in patent applications CN 201410211789.5 and CN 201510197279.1. FIG. 2 shows a flow chart of the solvent exchanging technique. As shown in FIG. 2, first, CTA is conveyed to a filtering zone in a rotary pressure filter by means of a slurry pump. In the filtering zone, part of impurities, such as acetic acid, catalyst and the like in the CTA are filtered out and conveyed to subsequent processes along with mother liquor. As a result, a filter cake is generated. Then, the filter cake after the filtering process is conveyed to washing zones along with rotation of the rotary pressure filter. According to processing requirements, the rotary pressure filter may be divided into N washing zones (N is an integer equal to or lager than 1). The washing process is performed in a reversed-flow manner. Specifically, each washing stage uses washing liquor discharged from a previous washing stage as washing liquor, except that the Nth washing stage uses fresh water as washing liquor. Washing liquor discharged from the first washing process is conveyed to a subsequent process through a first washing liquor pump. Then, the washed CTA filter cake is conveyed to an unloading zone to be unloaded to a pulping tank for pulping, and then conveyed to subsequent processes through a pulping pump. As compared to the above-mentioned processing technique using a centrifuge or a vacuum filter together with a steam pipe rotary dryer, this solvent exchanging technique has advantages of less equipments, and low energy consumption, and thus gradually becomes a common technique in the industry.

However, although the solvent exchanging technique with multiple stages of filtering and washing in a rotary pressure filter in a reversed-flow manner has the above advantages as compared with the prior art, it still has the following problems.

During PTA industrial production, the solvent exchanging technique generally includes five stages of reversed-flow washing. Correspondingly, the rotary pressure filter is generally includes a filtering zone, a first washing zone, a second washing zone, a third washing zone, a fourth washing zone, a fifth washing zone and an unloading zone. Since there are many zones in the rotary pressure filter, many sealing points are required to be provided in the rotary pressure filter, which increases fault points in the rotary pressure filter. Further, too many zones in the rotary pressure filter leads to small filtering area in each zone, which affects capacity of equipments, increases size and number of equipments, and also increases investment of equipments.

SUMMARY OF THE INVENTION

To solve the technical problem in the prior art, an object of the present invention is to provide a novel two-stages-three-step CTA solvent exchanging technique.

The present invention provides a CTA solvent exchanging method, comprising:

a filter cake forming step for separating mother liquor and CTA solid particles in CTA slurry to form a filter cake;

a first washing step for washing the filter cake in a first-step washing zone (7), and conveying the washed filter cake to a second-step washing zone (8);

a second washing step for washing the filter cake processed by the first washing step in the second-step washing zone (8), and conveying the washed filter cake to a third-step washing zone (9); and a third washing step for introducing external fresh water to the third-step washing zone (9) to wash the filter cake which has been washed in two washing steps, unloading and conveying the washed and qualified filter cake to a subsequent system, and distributing washing liquor discharged from the third washing step to a first-stage washing liquor tank (2) and a second-stage washing liquor tank (4) to be reused as washing liquor for the first washing step and the second washing step, respectively.

In the CTA solvent exchanging method according to the present invention, the filter cake forming step preferably includes a step of:

conveying the CTA slurry to a filtering zone (6) of a rotary pressure filter (1), separating the mother liquor and the CTA solid particles to form the filter cake in the filtering zone (6), and distributing the mother liquor to a subsequent system through a mother liquor zone (11).

In the CTA solvent exchanging method according to the present invention, the first washing step preferably includes a step of:

conveying the filter cake in the filtering zone (6) to the first-step washing zone (7) along with rotation of the rotary pressure filter (1), introducing washing liquor from the first-stage washing liquor tank (2) to the first-step washing zone (7) by means of a first-stage washing liquor pump (3) to wash the filter cake, conveying the washed filter cake to the second-step washing zone (8) along with rotation of the rotary pressure filter (1), and distributing the washing liquor after washing through a first-step washing liquor zone (12) and conveying it to a subsequent system together with the mother liquor.

In the CTA solvent exchanging method according to the present invention, the second washing step preferably includes a step of:

conveying the filter cake in the first-step washing zone (7) to the second-step washing zone (8) along with rotation of a rotary pressure filter (1), introducing washing liquor from the second-stage washing liquor tank (4) to the second-step washing zone (8) by means of a second-stage washing liquor pump (5) to wash the filter cake, conveying the washed filter cake to the third-step washing zone (9) along with rotation of the rotary pressure filter (1), and distributing the washing liquor after washing through a second-step washing liquor zone (13) and conveying it to a subsequent system together with the mother liquor and the washing liquor from the first-step washing zone.

In the CTA solvent exchanging method according to the present invention, the third washing step preferably includes a step of:

conveying the filter cake in the second-step washing zone (8) to the third-step washing zone (9) along with rotation of a rotary pressure filter (1), introducing the external fresh water to the third-step washing zone (9) to wash the filter cake, conveying the washed filter cake to an unloading zone (10) along with rotation of the rotary pressure filter (1), unloading and conveying the qualified filter cake to the subsequent system, and distributing the washing liquor after washing to the second-stage washing liquor tank (4) and the first-stage washing liquor tank (2) to be reused as washing liquor for the second-step washing zone (8) and the first-step washing zone (7), respectively, through a second-stage washing liquor zone (14) and a first-stage washing liquor zone (15).

In the CTA solvent exchanging method according to the present invention, preferably, the filter cake forming step includes a step of conveying the CTA slurry to the filtering zone (6) of the rotary pressure filter (1), separating the mother liquor and the CTA solid particles to form the filter cake in the filtering zone (6), and distributing the mother liquor to a subsequent system through a mother liquor zone (11);

the first washing step includes a step of conveying the filter cake in the filtering zone (6) to the first-step washing zone (7) along with rotation of the rotary pressure filter (1), introducing washing liquor from the first-stage washing liquor tank (2) to the first-step washing zone (7) by means of a first-stage washing liquor pump (3) to wash the filter cake, conveying the washed filter cake to the second-step washing zone (8) along with rotation of the rotary pressure filter (1), and distributing the washing liquor after washing through a first-step washing liquor zone (12) and conveying it to a subsequent system together with the mother liquor;

the second washing step includes a step of conveying the filter cake in the first-step washing zone (7) to the second-step washing zone (8) along with rotation of a rotary pressure filter (1), introducing washing liquor from the second-stage washing liquor tank (4) to the second-step washing zone (8) by means of a second-stage washing liquor pump (5) to wash the filter cake, conveying the washed filter cake to the third-step washing zone (9) along with rotation of the rotary pressure filter (1), and distributing the washing liquor after washing through a second-step washing liquor zone (13) and conveying it to a subsequent system together with the mother liquor and the washing liquor from the first-step washing zone; and the third washing step includes a step of conveying the filter cake in the second-step washing zone (8) to the third-step washing zone (9) along with rotation of a rotary pressure filter (1), introducing the external fresh water to the third-step washing zone (9) to wash the filter cake, conveying the washed filter cake to an unloading zone (10) along with rotation of the rotary pressure filter (1), unloading and conveying the qualified filter cake to the subsequent system, and distributing the washing liquor after washing to the second-stage washing liquor tank (4) and the first-stage washing liquor tank (2) to be reused as washing liquor for the second-step washing zone (8) and the first-step washing zone (7), respectively, through a second-stage washing liquor zone (14) and a first-stage washing liquor zone (15).

In the CTA solvent exchanging method according to the present invention, the rotary pressure filter (1) includes a drum which is divided into five zones of a filtering zone (6), a first-step washing zone (7), a second-step washing zone (8), a third-step washing zone (9), and an unloading zone (10).

In the CTA solvent exchanging method according to the present invention, the rotary pressure filter (1) includes a control head which is divided into six zones of a mother liquor zone (11), a first-step washing liquor zone (12), a second-step washing liquor zone (13), a second-stage washing liquor zone (14), a first-stage washing liquor zone (15) and a filter-cloth-reverse-blowing unloading zone (16).

The present invention is further explained as follows.

A method for improving CTA solvent exchanging efficiency according to the present invention comprises the steps of:

a. conveying CTA slurry from upstream to a filtering zone of a pressure filter 1 at a certain pressure, separating solid particles and acetic acid in the CTA slurry gradually along with rotation of the pressure filter 1 to form a filter cake in the filtering zone, distributing separated mother liquor through a control head of the pressure filter 1 and conveying it to a subsequent process;

b. conveying the filter cake formed in the filtering zone to a first-step washing zone 7 along with rotation of the pressure filter 1, pressurizing washing liquor from a first-stage washing liquor tank 2 with a first-stage washing liquor pump 3 and conveying it to the first-step washing zone 7, washing the filter cake continuously with the washing liquor in the first-step washing zone 7, conveying the washed filter cake to a second-step washing zone along with rotation of the pressure filter 1, distributing the washing liquor through the control head of the pressure filter 1 and conveying it to a subsequent process together with the mother liquor;

c. pressurizing washing liquor from a second-stage washing liquor tank 4 with a second-stage washing liquor pump 5 and conveying it to a second-step washing zone, washing the filter cake from the first-step washing zone 7 continuously with the washing liquor in the second-step washing zone, conveying the washed filter cake to a third-step washing zone along with rotation of the pressure filter 1, distributing the washing liquor through the control head of the pressure filter 1 and conveying it to a subsequent process together with the mother liquor and the washing liquor from the first-step washing zone;

d. introducing external washing water at a certain pressure to the third-step washing zone 9, washing the filter cake from the second-step washing zone continuously with the washing water in the third-step washing zone 9, conveying the washed and qualified filter cake to an unloading zone 10 along with rotation of the pressure filter 1, unloading the qualified filter cake by gravity and conveying it to a subsequent process, distributing the washing liquor generated in the third-step washing zone through the control head and dividing it into two parts, one part being conveyed to the first-stage washing liquor tank 2 to be used as the washing liquor for the first-step washing zone, and the other part being conveyed to the second-stage washing liquor tank 4 to be used as the washing liquor for the second-step washing zone;

e. the pressure filter including a drum which is divided into five zones of a filtering zone 6, a first-step washing zone 7, a second-step washing zone 8, a third-step washing zone 9 and an unloading zone 10, and a control head which is divided into six zones of a mother liquor zone 11 corresponding to the filtering zone 6, a first-step washing liquor zone 12 corresponding to the first-step washing zone 7, a second-step washing liquor zone 13 corresponding to the second-step washing zone 8, a first-stage washing liquor zone 15 and a second-stage washing liquor zone 14 corresponding to the third-step washing zone 9, and a filter-cloth-reverse-blowing unloading zone 16 corresponding to the unloading zone 10.

The present invention has the following advantageous effects.

As compared to the conventional technique with filtering and washing in a pressure filter in a reversed-flow manner, the present invention implements the washing process in a two-stage-three-step manner. That is, the filtering zone is divided into three zones of a first-step washing zone, a second-step washing zone and a third-step washing zone. Further, the washing liquor generated in the third-step washing zone is divided into two stages to be distributed to a first-step washing zone and a second-step washing zone, respectively. In this way, the present invention may decrease divisional zones in the pressure filter, reduce times of washing, and increasing area of each zone correspondingly.

(1) Reduction in times of washing may further shorten the processing flow of the CTA solvent processing technique, decrease investment of accessory equipment, and reduce energy consumption of system;

(2) Since divisional zones of the pressure filter are decreased and the area of each zone is correspondingly increased, the pressure drop of the filter cake during filtering and washing is reduced, thereby improving processing capacity of the pressure filter. For the same PTA capacity, as compared to the conventional processing technique, the present invention may reduce the number of pressure filters, and decrease the investment of the pressure filter equipments and the energy consumption of system.

REFERENCE SIGNS LIST

1 Rotary Pressure Filter
2 First-Stage Washing Liquor Tank
3 First-Stage Washing Liquor Pump
4 Second-Stage Washing Liquor Tank
5 Second-Stage Washing Liquor Pump
6 Filtering Zone
7 First-Step Washing Zone
8 Second-Step Washing Zone
9 Third-Step Washing Zone
10 Unloading Zone
11 Mother Liquor Zone
12 First-Step Washing Liquor Zone
13 Second-Step Washing Liquor Zone
14 Second-Stage Washing Liquor Zone
15 First-Stage Washing Liquor Zone
16 Filter-Cloth-Reverse-Blowing Unloading Zone

DETAILED DESCRIPTION OF THE INVENTION

The embodiments of the present invention are explicitly explained below. To facilitating to understand the technical solution of the present invention, embodiments are described below with detailed implementations and procedures. However, the extent of protection of the present invention is not limited to those embodiments. In the embodiments, the experimental method that is not described with specific implement conditions may be conducted with common conditions in the art.

The present invention may be implemented as a continuous pressure filter integrated with filtering, washing and drying that has been researched and produced by Tianhua Institute of Chemical Machinery and Automation Co., Ltd. (Patent No.: CN 2009 2 0144208.5).

Figure 1:
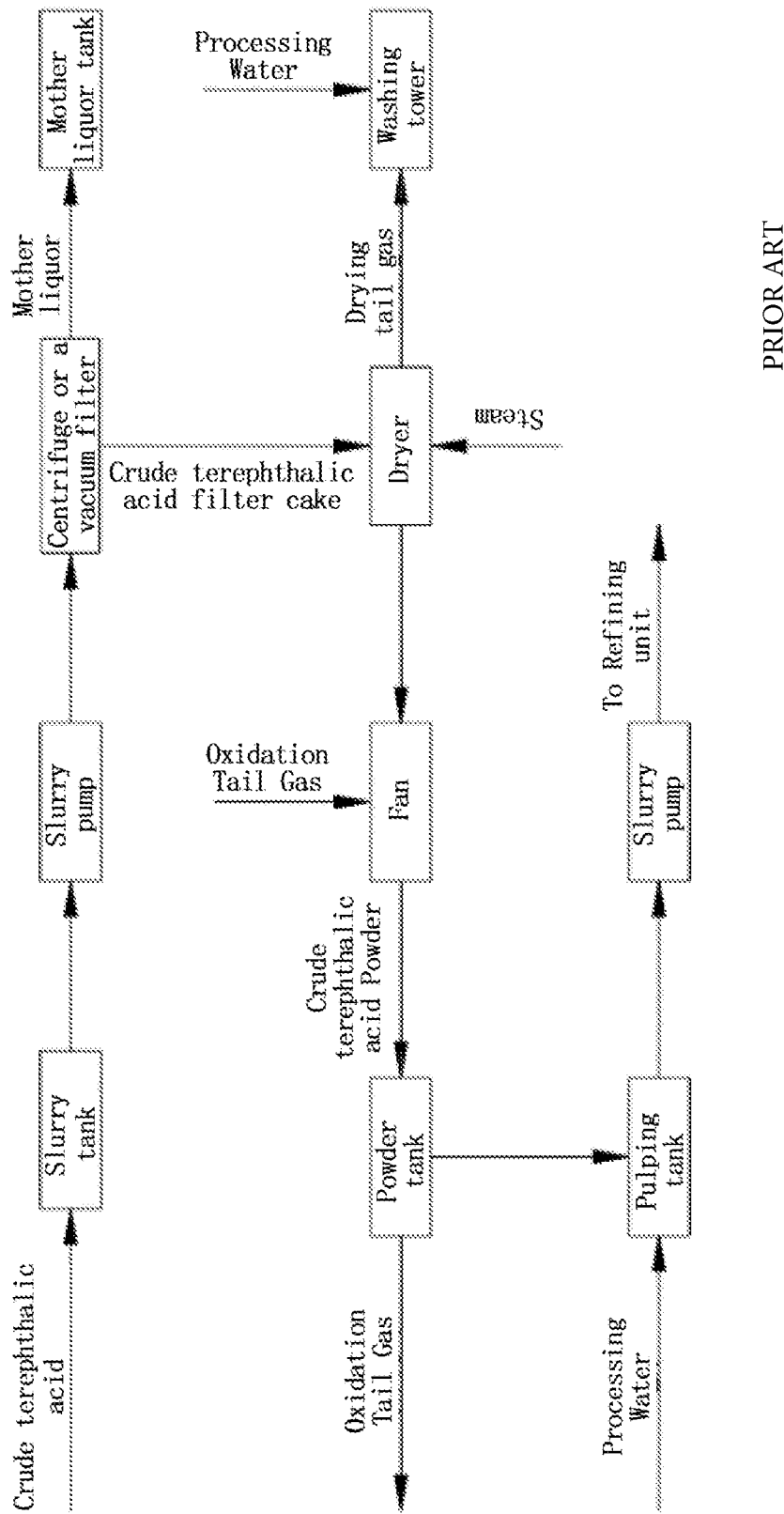
FIG. 1 is a flow chart showing a CTA processing system using a centrifuge or a vacuum filter of the prior art.
Figure 2:
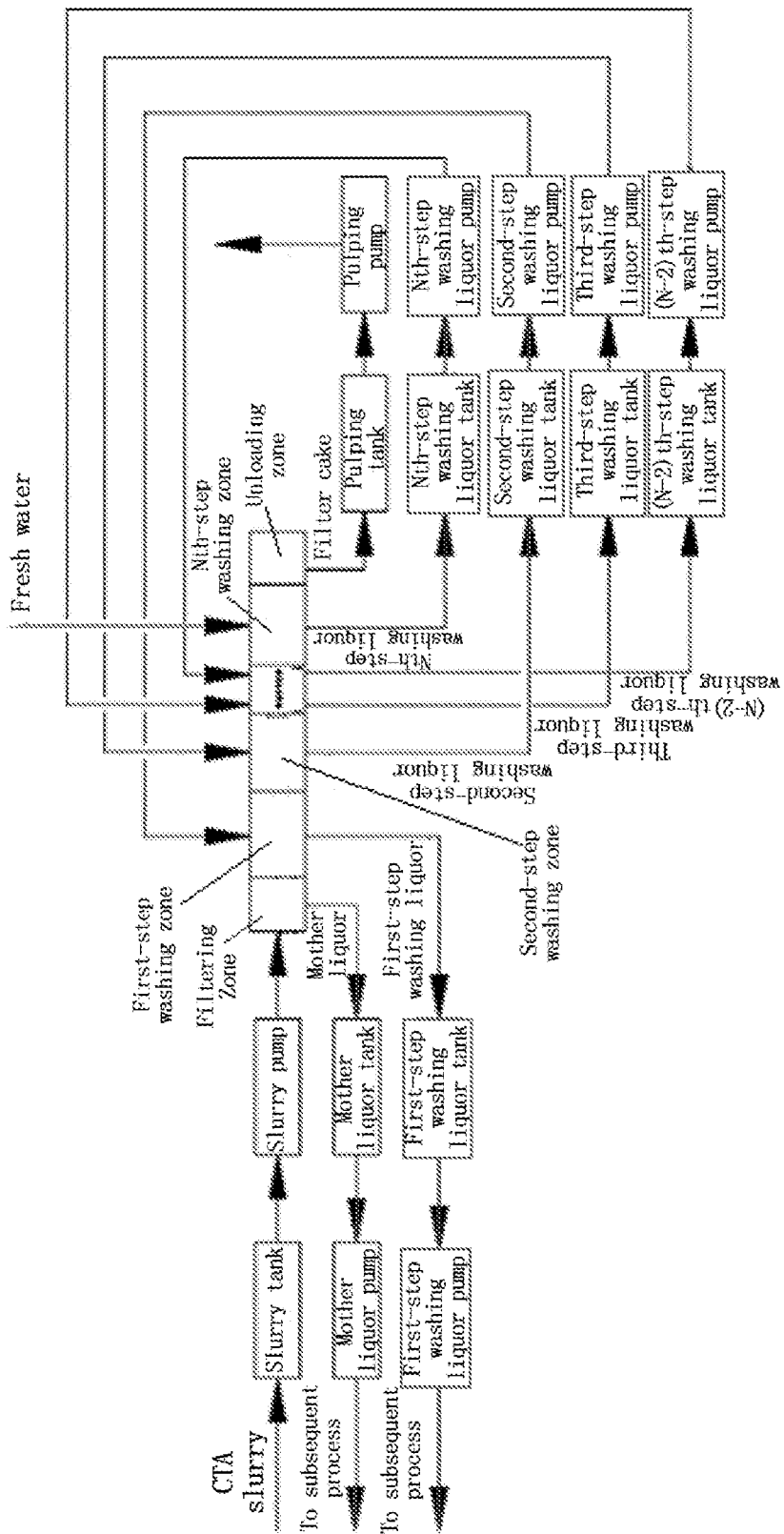
FIG. 2 is a flow chart showing a CTA processing technique with filtering and washing in a pressure filter in a reversed-flow manner of the prior art.
Figure 3:
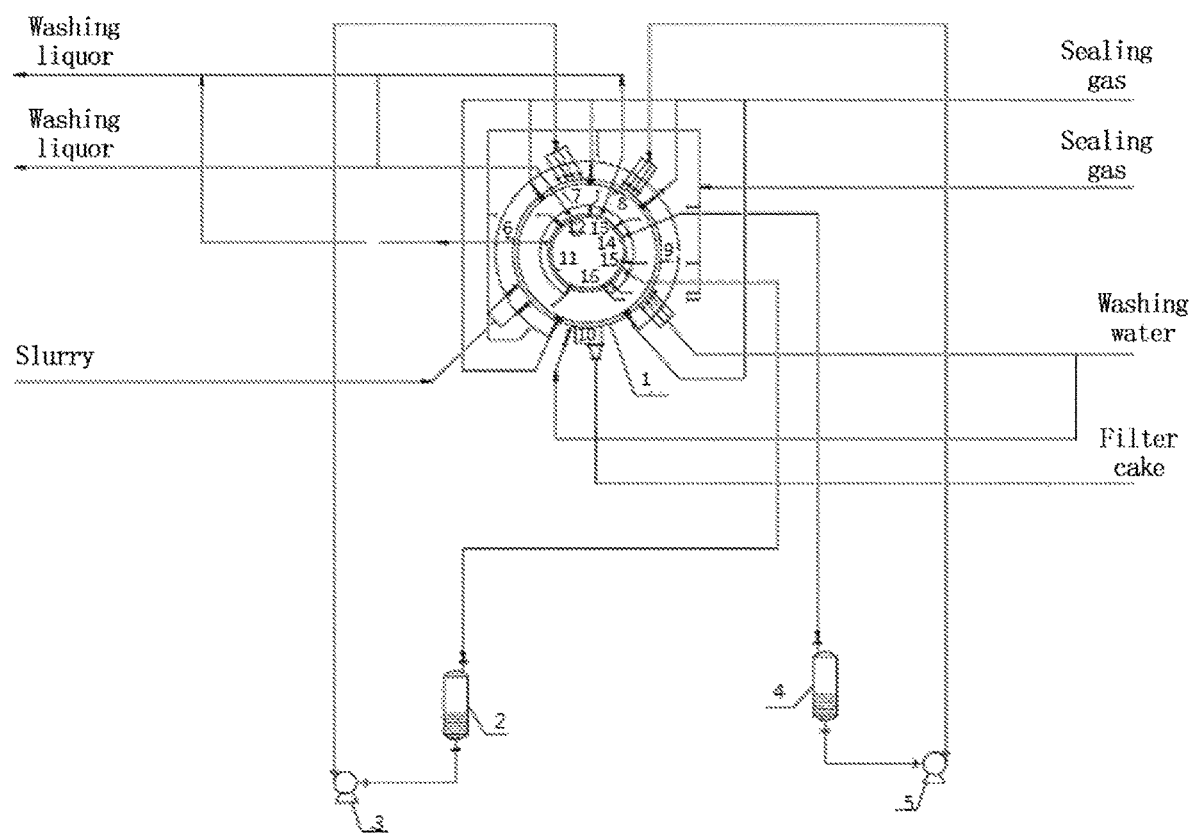
FIG. 3 is a diagram showing a process of the present invention.

As shown in FIG. 3, a novel two-stage-three-step solvent exchanging method includes the following steps.

(1) The pressure filter 1 includes a drum which is divided into five zones of a filtering zone 6, a first-step washing zone 7, a second-step washing zone 8, a third-step washing zone 9 and an unloading zone 10, and a control head which is divided into six zones of a mother liquor zone 11, a first-step washing liquor zone 12, a second-step washing liquor zone 13, a second-stage washing liquor zone 14, a first-stage washing liquor zone 15, and a filter-cloth-reverse-blowing unloading zone 16.

(2) CTA slurry from an upstream system at a certain pressure is conveyed to the filtering zone 6 of the pressure filter 1 to separate a mother liquor and CTA solid particles, and to form a filter cake in the filtering zone 6. The mother liquor is distributed to a subsequent system through the mother liquor zone 11 in the control head.

(3) The filter cake in the filtering zone 6 is conveyed to the first-step washing zone 7 along with rotation of the pressure filter 1. Washing liquor from a first-stage washing liquor tank 2 is conveyed to the first-step washing zone 7 by means of a first-stage washing liquor pump 3 to wash the filter cake. The washed filter cake is conveyed to the second-step washing zone 8 along with rotation of the pressure filter 1. The washing liquor after washing is distributed through the first-step washing liquor zone 12 of the control head and is conveyed to a subsequent system together with the mother liquor.

(4) The filter cake in the first-step washing zone 7 is conveyed to the second-step washing zone 8 along with rotation of the pressure filter 1. Washing liquor from a second-stage washing liquor tank 4 is conveyed to the second-step washing zone 8 by means of a second-stage washing liquor pump 5 to wash the filter cake. The washed filter cake is conveyed to the third-step washing zone 9 along with rotation of the pressure filter 1. The washing liquor after washing is distributed through the second-step washing liquor zone 13 of the control head and is conveyed to a subsequent system together with the mother liquor and the washing liquor from the first-step zone.

(5) The filter cake in the second-step washing zone is conveyed to the third-step washing zone 9 along with rotation of the pressure filter 1. External fresh water is introduced to the third-step washing zone 9 to wash the filter cake. The washed filter cake is conveyed to the unloading zone 10 along with rotation of the pressure filter. The qualified filter cake is unloaded and conveyed to a subsequent system. The washing liquor after washing is distributed through the second-stage washing liquor zone 14 and the first-stage washing liquor zone 15 of the control head and is conveyed to the second-stage washing liquor tank 4 and the first-stage washing liquor tank 2, respectively, to be used as the washing liquor for the second-step washing zone and the first-step washing zone.

What is claimed is:

1. A crude terephthalic acid (CTA) solvent exchanging method, comprising:
    a filter cake forming step for separating mother liquor and CTA solid particles in a CTA slurry to form a filter cake;
    a first washing step for washing the filter cake in a first-step washing zone, and conveying the washed filter cake to a second-step washing zone;
    a second washing step for washing the filter cake processed by the first washing step in the second-step washing zone, and conveying the washed filter cake to a third-step washing zone; and
    a third washing step for introducing external fresh water to the third-step washing zone to wash the filter cake which has been washed in two washing steps, unloading and conveying the washed and qualified filter cake to a subsequent system, and distributing washing liquor discharged from the third washing step to a first-stage washing liquor tank and a second-stage washing liquor tank to be reused as washing liquor for the first washing step and the second washing step, respectively.

2. The CTA solvent exchanging method according to claim 1, wherein the filter cake forming step includes a step of:
    conveying the CTA slurry to a filtering zone of a rotary pressure filter, separating the mother liquor and the CTA solid particles to form the filter cake in the filtering zone, and distributing the mother liquor to a subsequent system through a mother liquor zone.

3. The CTA solvent exchanging method according to claim 2, wherein the first washing step includes a step of:
    conveying the filter cake in the filtering zone to the first-step washing zone along with rotation of the rotary pressure filter, introducing washing liquor from the first-stage washing liquor tank to the first-step washing zone by means of a first-stage washing liquor pump to wash the filter cake, conveying the washed filter cake to the second-step washing zone along with rotation of the rotary pressure filter, and distributing the washing liquor after washing through a first-step washing liquor zone and conveying it to a subsequent system together with the mother liquor.

4. The CTA solvent exchanging method according to claim 3, wherein the second washing step includes a step of:
    after conveying the washed filter cake in the first-step washing zone to the second-step washing zone along with rotation of the rotary pressure filter, introducing washing liquor from the second-stage washing liquor tank to the second-step washing zone by means of a second-stage washing liquor pump to wash the filter cake, conveying the washed filter cake to the third-step washing zone along with rotation of the rotary pressure filter, and distributing the washing liquor after washing through a second-step washing liquor zone and conveying it to a subsequent system together with the mother liquor and the washing liquor from the first-step washing zone.

5. The CTA solvent exchanging method according to claim 4, wherein the third washing step includes a step of:
    after conveying the washed filter cake in the second-step washing zone to the third-step washing zone along with rotation of the rotary pressure filter, introducing the external fresh water to the third-step washing zone to wash the filter cake, conveying the washed filter cake to an unloading zone along with rotation of the rotary pressure filter, unloading and conveying the qualified filter cake to the subsequent system, and distributing the washing liquor after washing to the second-stage washing liquor tank and the first-stage washing liquor tank to be reused as washing liquor for the second-step washing zone and the first-step washing zone, respectively, through a second-stage washing liquor zone and a first-stage washing liquor zone.

6. The CTA solvent exchanging method according to claim 5, wherein the rotary pressure filter includes a drum which is divided into five zones: the filtering zone, the first-step washing zone, the second-step washing zone, the third-step washing zone, and the unloading zone.

7. The CTA solvent exchanging method according to claim 5, wherein the rotary pressure filter includes a control head which is divided into six zones: the mother liquor zone, the first-step washing liquor zone, the second-step washing liquor zone, the second-stage washing liquor zone, the first-stage washing liquor zone and the unloading zone, wherein the unloading zone is a filter-cloth-reverse-blowing.

* * * * *